(12) United States Patent
Tan et al.

(10) Patent No.: US 10,294,255 B1
(45) Date of Patent: *May 21, 2019

(54) MULTIFUNCTIONAL CROSSLINKING AGENT, CROSSLINKED POLYMER, AND METHOD OF MAKING SAME

(71) Applicant: The United States of America, as represented by the Secretary of the Air Force, Washington, DC (US)

(72) Inventors: Loon-Seng Tan, Centerville, OH (US); David Huabin Wang, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 24 days.

This patent is subject to a terminal disclaimer.

(21) Appl. No.: 15/009,360

(22) Filed: Jan. 28, 2016

Related U.S. Application Data (60) Provisional application No. 62/202,255, filed on Aug. 7, 2015.

(51) Int. Cl.
    *C07F 9/655* (2006.01)
    *C08G 73/10* (2006.01)

(52) U.S. Cl.
    CPC .......... *C07F 9/65517* (2013.01); *C08G 73/10* (2013.01)

(58) Field of Classification Search
    None
    See application file for complete search history.

(56) References Cited

U.S. PATENT DOCUMENTS

| | | | |
|---|---|---|---|
| 3,455,879 A | 7/1969 | Gay et al. | |
| 3,514,415 A | 5/1970 | Karol | |
| 3,600,361 A | 8/1971 | Heacock et al. | |
| 3,732,200 A | 5/1973 | Bach | |
| 3,763,211 A | 10/1973 | Heath et al. | |
| 3,835,120 A | 9/1974 | Bach et al. | |
| 3,925,312 A | 12/1975 | Fletcher | |
| 3,988,374 A | 10/1976 | Brode et al. | |
| 4,107,125 A | 8/1978 | Lovejoy | |
| 4,111,906 A | 9/1978 | Jones et al. | |
| 4,203,922 A | 5/1980 | Jones et al. | |
| 4,271,288 A | 6/1981 | Woo | |
| RE30,922 E | 5/1982 | Heilman et al. | |
| 4,394,499 A | 7/1983 | Robinson et al. | |
| 4,535,101 A | 8/1985 | Lee et al. | |
| 4,728,697 A | 3/1988 | Bolan et al. | |
| 4,797,466 A | 1/1989 | Oikawa et al. | |
| 4,981,497 A | 1/1991 | Hayes | |
| 5,101,005 A | 3/1992 | Vora et al. | |
| 5,101,037 A | 3/1992 | McGrath et al. | |
| 5,175,234 A | 12/1992 | Lubowitz et al. | |
| 5,205,894 A | 4/1993 | Ohta et al. | |
| 5,237,045 A | 8/1993 | Burchill et al. | |
| 5,278,276 A | 1/1994 | Ohta et al. | |
| 5,300,559 A | 4/1994 | Sheehan et al. | |
| 5,344,894 A | 9/1994 | Lubowitz et al. | |
| 5,411,765 A | 5/1995 | Kanakarajan et al. | |
| 5,508,377 A | 4/1996 | Yamashita et al. | |
| 5,516,876 A | 5/1996 | Lubowitz et al. | |
| 5,585,217 A | 12/1996 | Oba | |
| 5,599,582 A | 2/1997 | Adamopoulous et al. | |
| 5,610,265 A | 3/1997 | Tan et al. | |
| 5,631,377 A | 5/1997 | Matsuo et al. | |
| 5,670,651 A | 9/1997 | Tan et al. | |
| 5,705,574 A | 1/1998 | Lubowitz et al. | |
| 5,710,241 A * | 1/1998 | Haubs ................. | C07D 209/48 525/436 |
| 5,864,002 A | 1/1999 | Stephens et al. | |
| 5,891,581 A | 4/1999 | Simpson et al. | |
| 5,965,687 A | 10/1999 | Jensen | |
| 6,001,277 A | 12/1999 | Ichimura et al. | |
| 6,184,333 B1 | 2/2001 | Gray | |
| 6,262,223 B1 | 7/2001 | Meador et al. | |
| 6,307,008 B1 | 10/2001 | Lee et al. | |

(Continued)

FOREIGN PATENT DOCUMENTS

| | | |
|---|---|---|
| EP | 233069 | 8/1987 |
| EP | 333406 | 9/1989 |

(Continued)

OTHER PUBLICATIONS

Pyun, Eumi, et al., "Kinetics and mechanisms of thermal imidization of a polyamic acid studied by ultraviolet-visible spectroscopy", Macromolecules (1989), 22(3), 1174-83.

Sakamoto, Kenji, et al., "Highly Polarized Polymer-Based Light Emitting Diodes Fabricated by Using Very Thin Photoaligned Polyimide Layers," Journal of Applied Physics 107, 113108 (2010).

Sakamoto, Kenji, et al., "Light Exposure Dependence of Molecular Orientation of Glassy Polyfluorene Layers Formed on Photo-Aligned Polyimide Films," Colloids and Surfaces B: Biointerfaces 56, pp. 260-264 (2007).

Serak, S.V., et al., "Azobenzene liquid crystal polymer-based membrane and cantilever optical systems," Optics Express, vol. 17, No. 18 (Aug. 31, 2009), 15736-15746.

(Continued)

*Primary Examiner* — Ana L. Woodward
(74) *Attorney, Agent, or Firm* — AFMCLO/JAZ; Chastity Whitaker (57) ABSTRACT

A multifunctional crosslinking agent, a crosslinked polymer, and a method of making the same are disclosed. The multifunctional crosslinking agent, which may be used to crosslink amine-terminated polyamides, polyimides, or poly(amide-imide)s, includes three or four anhydride functional groups. The multifunctional crosslinking agent may be defined by a general chemical formula (I): $(Z-Ar-)_n-W$, wherein W represents an anhydride functional group that is directly or indirectly bonded to Ar; Ar represents an aryl group that is directly bonded to W; and n is equal to 3 when W is P=O or N, or n is equal to 4 when W is Si or a carbon moiety.

20 Claims, 6 Drawing Sheets

(56) References Cited

U.S. PATENT DOCUMENTS

| | | | |
|---|---|---|---|
| 6,379,809 B1 | 4/2002 | Simpson et al. | |
| 6,509,094 B1 | 1/2003 | Shah et al. | |
| 7,402,264 B2 | 7/2008 | Ounaies et al. | |
| 7,527,751 B2 | 5/2009 | Ounaies et al. | |
| 7,582,722 B1 | 9/2009 | Tan et al. | |
| 7,588,699 B2 | 9/2009 | Park et al. | |
| 7,507,472 B2 | 11/2009 | Ounaies et al. | |
| 7,678,873 B1 | 3/2010 | Tan et al. | |
| 7,906,043 B2 | 3/2011 | Connell et al. | |
| 7,935,414 B2 | 5/2011 | Ounaies et al. | |
| 7,972,536 B2 | 7/2011 | Connell et al. | |
| 8,034,893 B2 | 10/2011 | Akiba et al. | |
| 8,173,763 B1 | 5/2012 | Tan et al. | |
| 8,314,203 B2 | 11/2012 | Tsutsumi et al. | |
| 8,389,619 B1 | 3/2013 | Tan et al. | |
| 8,546,614 B1 | 10/2013 | Tan et al. | |
| 8,633,284 B2 | 1/2014 | Ronk et al. | |
| 8,785,589 B1 | 7/2014 | Tan et al. | |
| 8,791,227 B1 | 7/2014 | Tan et al. | |
| 2003/0064235 A1 | 4/2003 | Okawa et al. | |
| 2004/0233377 A1 | 11/2004 | Utsumi et al. | |
| 2005/0080229 A1 | 4/2005 | Deets et al. | |
| 2006/0057377 A1 | 3/2006 | Harrison et al. | |
| 2006/0217482 A1 | 9/2006 | Lukehart et al. | |
| 2006/0235194 A1 | 10/2006 | Kato | |
| 2006/0270825 A1 | 11/2006 | Angermeier et al. | |
| 2007/0106056 A1 | 5/2007 | Itatani | |
| 2007/0270562 A1 | 11/2007 | Yamada et al. | |
| 2007/0272124 A1 | 11/2007 | Tsutsumi et al. | |
| 2008/0025905 A1 | 1/2008 | Wang et al. | |
| 2008/0311303 A1 | 12/2008 | Naiki et al. | |
| 2009/0220722 A1 | 9/2009 | Wang | |
| 2010/0048745 A1 | 2/2010 | Yamada et al. | |
| 2011/0009513 A1 | 1/2011 | Chaudhary et al. | |
| 2011/0136061 A1 | 6/2011 | Itatani | |

FOREIGN PATENT DOCUMENTS

| | | |
|---|---|---|
| EP | 0529162 | 3/1993 |
| EP | 659802 | 6/1995 |
| EP | 397023 | 1/2009 |
| EP | 2380867 | 10/2011 |
| GB | 1147856 | 12/1967 |
| JP | 2005023151 | 1/2005 |
| JP | 2005154643 | 6/2005 |
| WO | 2007086487 | 2/2007 |
| WO | 2009013376 | 1/2009 |

OTHER PUBLICATIONS

Si, J., et al., "Thermosetting enhancement of the light-induced polar orientation stability of molecules in polymers," J. Appl. Phys. 85, 8018 (1999); doi: 10.1063/1370637.

Sroog, C.E., "Polyimides," Prog. Polym. Sci. 1991, 16, 561-694.

SRS Technologies and Mantech Materials, "Polyimides: CP1 and CP2 Film Properties," printed Jul. 9, 2012, 1 page, available at <http://www.mantechmaterials.com/_images/documents/3_8_doc.pdf>.

St. Clair, Anne K., et al. "Synthesis and Characterization of Essentially Colorless Polyimide Films," J. Polym. Mater. Sci Eng., vol. 51, pp. 62-66 (1984).

Straub, Daniel, "Lewis Structures of Boron Compounds Involving Multiple Bonding," J. Chem. Ed. 72(6) 494-497 (1995).

Tabiryan, N. et al., "Polymer film with optically controlled form and actuation," T. Optics Express 2005, 13, 7442-7448.

Usami, K., et al., "Improvement in photo-alignment efficiency of azobenzene-containing polyimide films," Thin Solid Films 2009, 518, 729-734.

Usami, K., et al., "Stability of Photo-Induced Alignment of Azobenzene-Containing Polyimides," Molecular Crystals and Liquid Crystals (2005) 438:1, 227/[1791]-236[1800].

Usami, Kiyoaki, et al., "Photo-Aligned Blend Films of Azobenzene-Containing Polyimides with and without Side-Chains for Inducing Inclined Alignment of Liquid Crystal Molecules," Journal of Applied Physics (2011), 110(4), 043522/1-043522/6.

Usami, Kiyoaki, et al., "Pretilt Angle Control of Liquid Crystal Molecules by Photoaligned Films of Azobenzene-Containing Polyimide with Different Content of Side-Chain," Journal of Applied Phyics 104, 113528 (2008).

Van Oosten, C.L., et al., "Bending Dynamics and Directionality Reversal in Liquid Crystal Network Photoactuators," Macromolecules 2008,41,8592-8596.

Van Oosten, C.L., et al., "Glassy photomechanical liquid-crystal network actuators for microscale devices," Eur. Phys. J. E, 2007, 23, 329-336.

Viswanathan, N.K., et al., "Surface relief structures on azo polymer films," J. Mater. Chem. 1999, 9, 1941-1955.

Wang, D.H., et al., "Nanocomposites Derived from a Low-Color Aromatic Polyimide (CP2) and Amine-Functionalized Vapor-Grown Carbon Nanofibers: In Situ Polymerization and Characterization," Macromolecules 2007, 40, 6100-6111.

Wang, David H., et al., "Photomechanical Response of Glassy Azobenzene Polyimide Networks" Macromolecules 2011, 44, pp. 3840-3846.

White, T.J., et al., "A high frequency photodriven polymer oscillator," J. Soft Matter 2008,4, 1796-1798.

Xie, Tao, "Recent advances in shape memory polymer," Polymer (2011), 52(22), 4985-5000.

Yager, K. G., et al., "Azobenzene Polymers as Photomechanical and Multifunctional Smart Materials," Intelligent Materials, Shahinpoor, M. and Schneider, H.-J., Eds., Royal Society of Chemistry: Cambridge, UK, 2008; pp. 424-446.

Yu, Y., et al., "Effect of Cross-linking Density on Photoinduced Bending Behavior of Oriented Liquid-Crystalline Network Films Containing Azobenzene," Chem. Mater. 2004, 16, 1637-1643.

Yu, Y., et al., "Photomechanical Effects of Ferroelectric Liquid-Crystalline Elastomers Containing Azobenzene Chromophores," Angew. Chem., Int. Ed. 2007, 46, 881-883.

Yu, Y., et al., "Precisely Direction-Controllable Bending of Cross-Linked Liquid-Crystalline Polymer Films by Light," Mol. Cryst. Liq. Cryst., vol. 436, pp. 281/[1235]-290[1244], 2005.

Zhang, Chaohui, et al., "Rapid bending of a nonliquid crystal azobenzene polymer film and characteristics of surtace relief grating" Journal of Applied Polymer Science (2009), 113(2), 1330-1334.

Tan, Loon-Seng, et al., U.S. Appl. No. 13/546,439, filed Jul. 11, 2012.

Tan, Loon-Seng, et al., U.S. Appl. No. 13/557,326, filed Jul. 25, 2012.

Tan, Loon-Seng, et al., U.S. Appl. No. 13/661,194, filed Oct. 26, 2012.

Tan, Loon-Seng, et al., U.S. Appl. No. 13/866,524, filed Apr. 19, 2013.

Tan, Loon-Seng, et al., U.S. Appl. No. 13/866,823, filed Apr. 19, 2013.

Machine Translation of JP 2005023151.

Machine Translation of JP 2005154643.

Machine translation of WO 2009013376.

Shukla, H.M., et al. "Azo Group Containing Bis Ligand and its Coordination Polymers," Chem. Sci. Trans. 2013, 2(1), 301-307.

Felton, Samuel M.; Tolley, Michael T.; Shin, ByungHyun; Onal, Cagdas D.; Demaine, Erik D.; Rus, Daniela; and Wood, Robert J.; "Self-Folding with Shape Memory Composites." Soft Matter 9, No. 32 (2013): 7688.

Agolini, F., et al., "Synthesis and Properties of Azoaromatic Polymers," Macromolecules (May-Jun. 1970), vol. 3, No. 3, 349-351.

Amaranatha Reddy et al., "Occurrence of the B7 mesophase in two homologous series of seven-ring achiral compounds composed of banana-shaped molecules," Liq. Cryst., vol. 30 (2003) 273-283.

Arlen, M., et al., "Thermal-Electrical Character of in Situ Synthesized Polyimide-Grafted Carbon Nanofiber Composites," Macromolecules 2008, 41, 8053-8062.

Barrett, C.J., et al., "Photo-mechanical effects in azobenzene-containing soft materials," Soft Matter 2007, 3, 1249-1261.

(56) References Cited

OTHER PUBLICATIONS

Behl, Marc, et al., "Shape-memory polymers" Materials Today (Oxford, United Kingdom) (2007), 10(4), 20-28.
Cain, J. C., "Para- and Meta-nitrosoacetanilide," J. Chem. Soc., Trans. 1908, 93, 681-684.
Chao, Tsung-Yi, et al., "Nonlinear Optical Polyimide/Montmorillonite/ Nanocomposites Consisting of Azobenzene Dyes," Dyes and Pigments, 77 (2008) 515-524.
Chen, J.P., et al., "Highly Stable Optically Induced Birefringence and Holographic Surface Gratings on a New Azocarbazole-Based Polyimide," Macromolecules 1999, 32, 8572-8579.
Cojocariu, C., et al., "Light-induced motions in azobenzene-containing polymers," Pure Appl. Chem. 2004, 76, 1479-1497.
Eisenbach, C. D., "Relation between Photochromism of Chromophores and Free Volume Theory in Bulk Polyers," Ber. Bunsenges. Phys. Chem. 1980, 84, 680.
Eisenbach, C.D., "Isomerization of aromatic azo chromophores in poly(ethyl acrylate) networks and photomechanical effect," Polymer 1980, 21, 1175-1179.
Fay, Catherine C. et al., "Molecularly Oriented Polymeric Thin Films for Space Applications," High Performance Polymers, vol. 11, 145-156 (1999).
Finkelmann, H., et al., "A New Opto-Mechanical Effect in Solids," Phys. Rev. Lett 2001, 87, 01550111-01550114.
Georgiev, A., et al, "Polyimide Coatings Containing Azo-Chromophores as Structural Units," Journal of Physics, Conference Series vol. 113 No. 1 (2008) 012032.
Gonzalo et al., "Synthesis, Characterization, and Thermal Properties of Piezoelectric Polyimides," J. Polym. Sci. Part A: Polym. Chem., vol. 47 (2009) 722-730.
Harris, K.D., et al., Large amplitude light-induced motion in high elastic modulus polymer actuators, J. Mater. Chem. 2005, 15, 5043-5048.
He, Guang S., et al., "Degenerate Two-Photon-Absorption Spectral Studies of Highly Two-Photon Active Organic Chromophores," J. Chem. Phys., vol. 120 No. 11 (2004) 5275-5284.
Hergenrother, P.M., "Recent Developments in High Temperature Organic Polymers," Polyimides and Other High-Temperature Polymers, Abadie, M.J.M. and Sillion, B., Eds., Elsevier: New York, 1991, pp. 1-18.
Hogan, P.M., et al., "UV-Manipulation of Order and Macroscopic Shape in Nematic Elastomers," Phys. Rev. E: Stat., Nonlinear, Soft Matter Phys. 2002, 65, 041720/1-041720110.
Hosono, Nobuhiko, et al., "Photochemical control of network structure in gels and photo-induced changes in their viscoelastic properties" Colloids and Surfaces, B: Biointerfaces (2007), 56(1-2), 285-289.
Hrozhyk, Uladzimir, et al., "Bidirectional Photoresponse of Surface Pretreated Azobenzene Liquid Crystal Polymer Networks," Optics Express, vol. 17, Issue 2, pp. 716-722 (2009).
Hugel, Thorsten, et al., "Single-molecule optomechanical cycle", Science (2002), 296(5570), 1103-1106.
Irie, M, et al., "Photoresponsive Polymers," Functional Monomers and Polymers, 2nd ed., Takemoto, K., et al., Eds., Dekker: New York, 1997, pp. 65-116.
Irie, M., "Photochromism and Molecular Mechanical Devices," Bull. Chem. Soc. Jpn. 2008, 81 (8), 917-926.
Jacobs et al., "Dielectric characteristics of polyimide CP2," Polym., vol. 51 (2010) 3139-3146.
Japanese Patent Office, Machine Translation of JP 2005154643A, 39 pages.
Jenekhe, Samson A., et al., Nonlinear Optical Properties of Poly(p-phenylenebenzobisoxazole), Chem. Mater. 1992, 4, 683-687.

Kannan, Ramamurthi, et al., Diphenylaminofluorene-Based Two-Photon Absorbing Chromophores with Various π-Electron Acceptors, Chem. Mater. 2001, 13, 1896-1904.
Kannan, Ramamurthi, et al., "Toward Highly Active Two-Photon Absorbing Liquids: Synthesis and Characterization of 1,3,5-Triazine-Based Octupolar Molecules," Chem. Mater. 2004, 16, 185-194.
Koerner, H., et al., "Photogenerating work from polymers," Mater. Today (Oxford, U. K.) 2008, 11, (7-8), 34-42.
Koerner, Koerner, et al., "Polymer design for high temperature shape memory: Low crosslink density polyimides," Polymer(2013), 54, 391-402.
Kondo, M., et al., "Effect of concentration of photoactive chromophores on photomechanical properties of crosslinked azobenzene liquid-crystalline polymers," J. Mater. Chem. 2010, 20, 117-122.
Koshiba, Y., et al., "Photo-induced alignment behavior of azobenzene compound in thin film," Thin Solid Films 2009, 518, 805-809.
Kumar, G.S., et al., "Photochemistry of Azobenzene-Containing Polymers," Chem. Rev. 1989, 89, 1915-25.
Lee et al., "Enhancement of photogenerated mechanical force in azobenzene-functionalized polyimides," Angew. Chem., vol. 124 (2012) 4193-4197.
Lee, K.M., et al., "Relationship between the Photomechanical Response and the Thermomechanical Properties of Azobenzene Liquid Crystalline Polymer Networks," Macromolecules 2010, 43, 8185-8190.
Lee, Kyung Min, and White, Timothy J., "Photomechanical Response of Composite Structures Built from Azobenzene Liquid Crystal Polymer Networks," Polymers (2011), 3, 1447-1457.
Lendlein Andreas et al., "Shape-Memory Polymers," Angewandte Chemie, International Edition, vol. 41, 2034-2057 (2002).
Li, M.-H., et al., "Light-Driven Side-On Nematic Elastomer Actuators," Adv. Mater. 2003, 15, 569-572.
Liu C et al., "Review of Progress in Shape-Memory Polymers," Journal of Materials Chemistry, vol. 17, 1543-1558 (2007).
Lovrien, R., "The Photoviscosity Effect," Proc. Natl. Acad. Sci. U.S. A. 1967 (57) 236-242.
Makita, Shohei, et al., "Synthesis of Alkaline-Developable, Photosensitive Hyperbranched Polyimides through the Reaction of Carboxylic Acid Dianhydrides and Trisamines," Journal of Polymer Science Part A: Polymer Chemistry, vol. 42, 3697-3707 (2004).
Mathisen R. et al., "Imidization studies of polyamic acids by dye-labeling technique," Polymer Preprints (American Chemical Society, Division of Polymer Chemistry) (1987), 28(1), 82-83.
Meador, Mary Ann B., et al., "Improvements to the Synthesis of Polyimide Aerogels," ACS Spring National Meeting 2011, Anaheim, CA; Mar. 20-26, 2011, 34 pages.
Meador, Mary Ann B., et al., "Synthesis and Properties of Nanoporous Polyimide Aerogels Having a Covalently Bonded Network Structure," Polymer Preprints 2010, 51(1), 265.
Miner, Gilda A., et al., "The Wettability of LaRC Colorless Polyimide Resins on Casting Surfaces," J. Polym. Mater. Sci Eng., vol. 76, pp. 381-382 (1997).
Vatansohn, A., et al., "Photoinduced Motions in Azo-Containing Polymers," Chemical Reviews (Washington, DC, United States) (2002), 102(11), 4139-4175.
Park, B., et al., "Thermal and Optical Stabilities of Photoisomerizable Polyimide Layers for Nematic Liquid Crystal Alignments," Jpn. J. Appl. Phys. vol. 37 (1998) pp. 5663-5668.
Park, C., et al., "Actuating Single Wall Carbon Nanotube—Polymer Composites: Intrinsic Unimorphs," Adv. Mater. 2008, 20, 2074-2079.
Pieroni, O., et al., "Photoresponsive Polymeric Materials," Trends Polym. Sci. (Cambridge, U.K.) 1995, 3, 282-287.

* cited by examiner

Crosslinked Polyimide films containing three-arm phosphine-oxide (P=O) net points designated by the "wavy bond"; : DP of each arm designated by n,m,l

FIG. 6

MULTIFUNCTIONAL CROSSLINKING AGENT, CROSSLINKED POLYMER, AND METHOD OF MAKING SAME

CROSS-REFERENCE TO RELATED APPLICATIONS

The present application claims priority to U.S. Provisional Patent Application Ser. No. 62/202,255, which was filed on Aug. 7, 2017 and is incorporated herein by reference in its entirety. This application is also related to co-pending U.S. patent application Ser. No. 15/009,356, filed on even date herewith, by inventor Loon-Seng Tan, et al., and entitled, "METHOD OF FABRICATING SHAPE MEMORY FILMS," which is incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The invention generally relates to multifunctional cross-linking agents and the cross-linked polymers made therefrom. More particularly, the invention relates to tri-anhydride and tetra-anhydride crosslinking agents that may be used to form crosslinked polyimide, polyamide, and poly(amide-imide) polymers and films having shape memory properties at elevated temperatures and methods of making the same.

BACKGROUND OF THE INVENTION

Shape memory polymers (SMPs) are a class of active materials that can be programmed to "fix" a temporary shape or a series of temporary shapes, and then later to recover to a "memorized" permanent shape established by a covalent or physical network by applying thermal, electrical, or other environmental stimulus. In the case of thermal stimulation, the shape memory polymers are characterized by deforming at a temperature above a softening transition such as glass transition temperature ($T_g$) and melting point ($T_m$) of the polymer, then cooling through this transition under stress, causing immobilization of the constituent network chains, and the macroscopic shape to be fixed. Recovery of the permanent shape is then accomplished by heating above the triggering temperature, which re-mobilizes the network chains and allows rubber (entropic) elasticity to return the sample to its equilibrium shape. Depending on the nature of external stimulus, SMPs are categorized as the thermally-induced SMPs, light-induced SMPs, electro-active SMPs, pH-responsive SMPs, and water/moisture-driven SMPs, and various mechanisms are operating in each category. Shape-memory materials, which include shape-memory alloys (SMAs), have been widely used in actuation, aircraft, robotics, piping, medical, and dental applications. It is noted that SMPs differ from SMAs in that their glass transition or melting transition from a hard to a soft phase, which is responsible for driving the shape memory effect, whereas for SMAs, martensitic/austenitic transitions are responsible for the shape memory effect.

There are numerous advantages that make SMPs more attractive than SMAs. For example, SMPs have much higher capacities for elastic deformation (up to 200% in most cases), much lower cost, lower density, a broader range of application temperatures which can be tailored, comparatively easy processing, and potential biocompatibility and biodegradability. However, the state-of-the art SMPs are consisted of high-alkyl content polymers such as, polyurethane, poly(ε-caprolactone), poly(norbornene), (ethylene-oxide)/(ethylene terephthalate)-based copolymers, styrene/butadiene copolymers, thiol-ene/acrylate copolymers, etc. Therefore, none of the foregoing has shape-memory properties temperatures above 150° C. or long-term thermal and thermo-oxidative stabilities at this temperature region.

In recent years, a number of high-temperature shape-memory polymers have appeared in open and patent literature. For example, aromatic polyimides, polyamides, and poly(amide-imide)s are common classes of heat-resistant, thermally stable, polymers with glass transition temperatures in excess of 150° C., and have been crosslinked with multifunctional amine crosslinking agents to impart shape-memory effects, as described in U.S. Pat. Nos. 8,546,614; 8,791,227; and 8,962,890, each of which is incorporated herein by reference in its entirety. However, the multifunctional amine crosslinking agents are limited to polymers bearing amine-reactive groups.

In view of the foregoing, there is a need for new multifunctional crosslinking agents and methods of making and using same to impart shape-memory effects to the parent polymers.

SUMMARY OF THE INVENTION

In accordance with embodiments of the present invention, a multifunctional crosslinking agent comprising a plurality of anhydride functional groups is provided. The multifunctional crosslinking agent may be defined by a general chemical formula (I): Z—(—Ar—)$_n$—W, wherein W represents an anhydride functional group that is directly bonded to Ar; Ar represents an aryl group that is directly bonded to W; and n is equal to 3 when W is P=O or N, or n is equal to 4 when W is Si or a carbon moiety. In an embodiment, a tri-anhydride crosslinking agent may be Z—(—Ar—)$_3$N or Z—(—Ar—)$_3$P=O. In another embodiment, a tetra-anhydride crosslinking agent may be Z—(—Ar—)$_4$Si or Z—(—Ar=)$_4$R, where R represents the carbon moiety (e.g., a fluorenyl group). In another embodiment, a method of synthesizing the multifunctional crosslinking agent is provided.

In accordance with yet another embodiment of the present invention, a cross-linked polymer composition is provided. The crosslinked polymer composition comprising at least one of a polyamide, a polyimide, a poly(amide-imide), or mixtures thereof is cross-linked by the multifunctional cross-linking agent described herein.

Additional objects, advantages, and novel features of the invention will be set forth in part in the description and drawings which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the invention and, together with the summary given above, and the detailed description given below, serve to explain the invention.

FIG. 6 illustrates an exemplary synthetic scheme toward producing crosslinked polyimides using an exemplary phosphine oxide-based tri-anhydride crosslinking agent 1a.

DETAILED DESCRIPTION OF THE INVENTION

Embodiments of the present invention overcome an existing need in the prior art by providing a multi-anhydride crosslinking agent, which is suitable to crosslink polyimide, polyamide, and poly(amide-imide) polymers. Accordingly, the composition and synthesis of a new family of multi-anhydride containing crosslinking agents, as well as the corresponding crosslinked polymers, are described herein. The disclosed crosslinking agents are useful toward imparting shape-memory effects to heat-resistant polymers, (e.g., polyimides, polyamides and poly(amide-imides). More specifically, embodiments of the present invention relate to multi-anhydride compounds that may be used to crosslink polyimides, polyamides, and poly(amide-imides) to create covalent network structure that results in shape memory effects at elevated temperatures.

Multi-Anhydride Crosslinking Agents

In accordance with embodiments of the present invention, a multifunctional crosslinking agent is provided that has three or four anhydride functional groups (i.e., tri-anhydride crosslinking agents or tetra-anhydride crosslinking agents, respectively). The multifunctional crosslinking agents may be defined by the general chemical formula (I): Z—(—Ar—)$_n$W, wherein Z represents an anhydride functional group that is directly or indirectly bonded to Ar; wherein Ar represents an aryl group that is directly bonded to W; and wherein n is equal to 3 when W is N or P═O, or n is equal to 4 when W is Si or an $sp^3$ hybridized carbon moiety. Accordingly, the tri-anhydride crosslinking agents may be Z—(—Ar—)$_3$N or Z—(—Ar—)$_3$P═O; and the tetra-anhydride crosslinking agents may be Z—(—Ar—)$_4$Si or Z—(—Ar—)$_4$R, where R represents the carbon moiety (e.g., fluorenyl).

In accordance with an aspect of the invention, the aryl group (Ar), which is directly bonded to W through a carbon atom, may be a phenyleneoxy group (—OPh-) that is para- or meta-substituted with respect to oxygen, and thus the agent may be further defined by the general chemical formula (II): Z—(—OPh-)$_n$—W. In one embodiment, the phenyleneoxy group represents that the benzene ring portion may unsubstituted (i.e., OC$_6$H$_4$); alternatively, the phenyleneoxy group may have substituents (e.g., C1-C4 alkyl groups) around the benzene ring. In one example, where W is P═O, the agent may be further defined by the general chemical formula (III): Z—(—OPh-)$_3$-P═O.

In accordance with another aspect, the aryl group (Ar) may be a phenyleneoxy group (—OPh-) that is para- or meta-substituted with respect to oxygen, and Z may be a phthalic anhydride group that is connected to the phenyleneoxy group through an ether bond. Accordingly, the agent may be further defined by the general chemical formula (IVa):

wherein W and n are as defined above, and $R^1$ through $R^8$ are independently selected from H or C1-C4 alkyl. Where W is P═O, these phosphine oxide-based crosslinking agents may be defined by the general chemical formula (IV):

As shown in Table 1 (below), where $R^1$ to $R^3$ and $R^5$ to $R^8$ are H, an exemplary phosphine oxide-based crosslinking agent is tris[4-(3,4-dicarboxyphenoxy)phenyl] phosphine oxide tri-anhydride (1a). An isomeric phosphine oxide-based crosslinking agent to (1a) is its meta-isomer, which is tris[3-(3,4-dicarboxyphenoxy)phenyl] phosphine oxide tri-anhydride (i.e., $R^1$ to $R^4$ and $R^6$ to $R^8$ are H, see FIG. 1, agent 1b).

Figure 1:
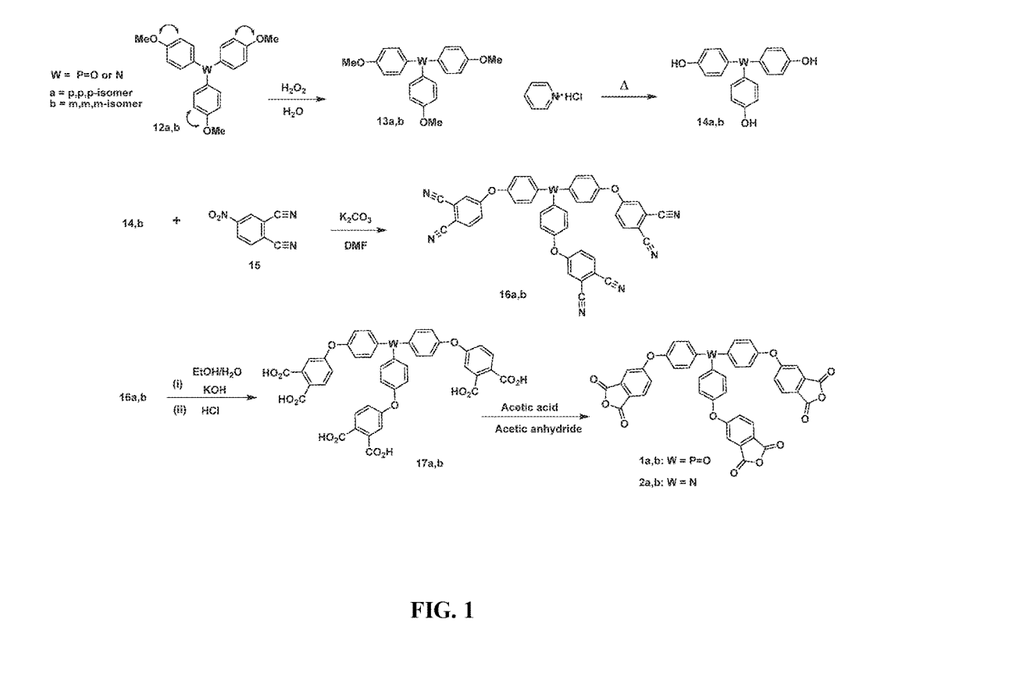
FIG. 1 illustrates an exemplary synthetic scheme toward producing phosphine oxide-based tri-anhydride crosslinking agent 1a,b and amine-based tri-anhydride crosslinking agent 2a,b.

The synthesis of the para- and meta-isomers of (1a,b) are depicted in FIG. 1. The synthesis of the para-isomer of triphenylphosphine oxide tri-anhydride (i.e., 1a) has been accomplished in 5-steps starting from commercially available tris(4-methoxyphenyl)phosphine oxide and experimental details are provided in the Examples. Briefly and with reference to FIG. 1, tris(4-methoxyphenyl)phosphine (12) was oxidized to tris(4-methoxyphenyl)phosphine oxide (13). While BBr$_3$ may be used to de-methylate compound (13), demethylation with pyridine hydrochloride above its melting point was observed to be more effective and cleaner. Nucleophilic substitution reaction of the resulting tris(4-hydroxyphenyl)phosphine oxide (14) with 4-nitro-phthalonitrile (15) after deprotonation in situ by potassium carbonate) in DMF afforded the corresponding tris(ether di-nitrile) compound, namely tris[4-(3,4-dicyanophenoxy)phenyl] phosphine oxide (16). Upon subsequent alkaline hydrolysis, (16) was converted to the corresponding tris(ether diacid) (17), which was then cyclo-dehydrated to produce the desired tri-anhydride monomer (1a). The meta,meta,meta-isomer (1b) of crosslinker (1a) can be prepared following the same synthetic sequence starting from tris(3-methoxyphenyl)phosphine (12b).

In accordance with yet another aspect, where W is N, and where the aryl group (Ar) is the phenyleneoxy group (—OPh-), which is para- or meta-substituted with respect to oxygen, a tertiary amine-based crosslinking agent may be defined by the general chemical formula (V): Z—(—OPh-)$_3$N. In another embodiment, where Z is the phthalic anhydride group that is connected to the phenyleneoxy group through an ether bond, exemplary tertiary amine-based crosslinking agents may be defined by the general chemical formula (VI):

As shown in Table 1 (below), where $R^1$ to $R^3$ and $R^5$ to $R^8$ are H, an exemplary tertiary amine-based crosslinking agent is tris[4-(3,4-dicarboxyphenoxy)phenyl]amine tri-anhydride (2a). An isomeric tertiary amine-based crosslinking agent to compound (2a) is its meta-isomer, which is tris[3-(3,4-dicarboxyphenoxy)phenyl]amine tri-anhydride (i.e., $R^1$ to $R^4$ and $R^6$ to $R^8$ are H, see FIG. 1, agent (2b)).

An amenable synthesis for the para- and meta-isomers of (2a,b) is also depicted in FIG. 1. Starting from tris(4-methoxyphenyl)amine or tris(3-methoxyphenyl)amine, the desired tri-anhydride tertiary amine-based crosslinking agents (2a,b) may be realized.

In accordance with yet another aspect where W is nitrogen (N), and where Z and Ar from Formula (I) in combination form a phthalic anhydride moiety that is directly bonded to nitrogen, this tertiary amine-based crosslinking agent may be defined by the general formula (VII):

wherein $R^9$ to $R^{11}$ are independently selected from H or C1-C4 alkyl. As shown in Table 1 (below), where $R^9$ through $R^{11}$ are H, an exemplary tertiary amine-based crosslinking agent is tris(phthalic anhydride)amine (3) (see also FIG. 2).

Figure 2:
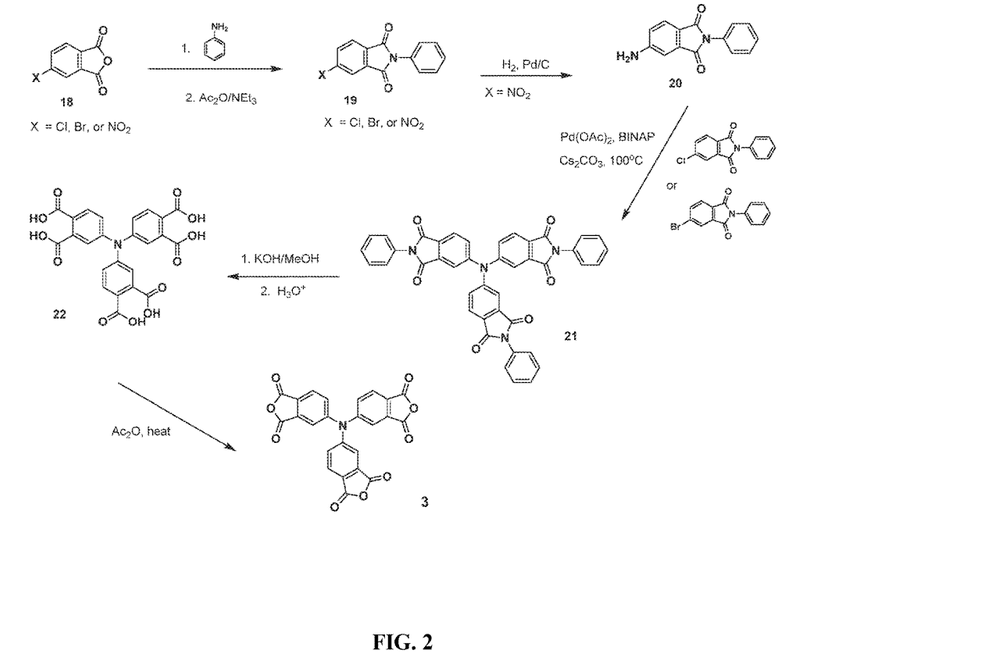
FIG. 2 illustrates an exemplary synthetic scheme for producing amine-based tri-anhydride crosslinking agent 3.

As shown in FIG. 2, an amenable synthetic sequence toward making tris(phthalic anhydride)amine (3) starts with a two-step imidization reaction of commercially available 4-halophthalic anhydride (18, X=Cl or Br) and/or 4-nitrophthalic anhydride (18, X=NO$_2$) with aniline in a polar solvent, followed by addition of acetic anhydride and trimethylamine, which would afford the 4-substituted N-phenylphthalimide compound (19). For compound (19), (with X=NO$_2$), the nitro group can be reduced under standard hydrogenation conditions to afford N-phenyl 4-aminophthalimide (20). Following a method derived from Wenmu Li et al. (*Macromolecules* 2007, 40, 8205-8211), 4-aminophthalimide (20) can be twice N-arylated with two equivalents of N-phenyl-4-halophthalimide (19, X=Cl or Br) with an in situ-generated catalyst from palladium acetate, and a phosphine ligand. For N-phenyl-4-bromophthalimide, a preferred phosphine ligand is BINAP=2,2'-bis(diphenylphosphino)-1,1'-binaphthyl, and for N-phenyl-4-chlorophthalimide, a preferred phosphine ligand is tert-butyldiphenylphosphine ($^t$BuPh$_2$P). The resulting tris(phthalimide)amine intermediate (21) can be readily hydrolyzed under alkaline conditions to generate the corresponding tris(phthalic acid)amine intermediate (22), which upon treatment with acetic anhydride/acetic/heat will lead to the desired tri-anhydride crosslinking agent (3).

TABLE 1

Exemplary Multi-Anhydride Crosslinking Agents

Tri-anhydride crosslinkers

1a

TABLE 1-continued

Exemplary Multi-Anhydride Crosslinking Agents

2a

3

Tetra-anhydride crosslinkers 4a (n = 0)
4b (n = 1)

TABLE 1-continued

Exemplary Multi-Anhydride Crosslinking Agents 5a (E = Si; all para)
5b (E = Si; all meta)
5c (E = C; all para)

In accordance with another embodiment, complementary tetra-anhydride crosslinking agents include where W (in Formulas (I), (II), and (IVa)) is a carbon moiety, and thus n is 4. Further, exemplary carbon-based tetra-anhydride crosslinking agents (4a), (4b), and 5(c) are also shown in Table 1. The carbon moiety may include a centralized $sp^3$ hybridized carbon to provide a generally tetrahedral geometry to the agent. For example, agents 4a and 4b include a fluorenyl group, where the C9 carbon of the fluorenyl group is $sp^3$ hybridized.

Figure 3:
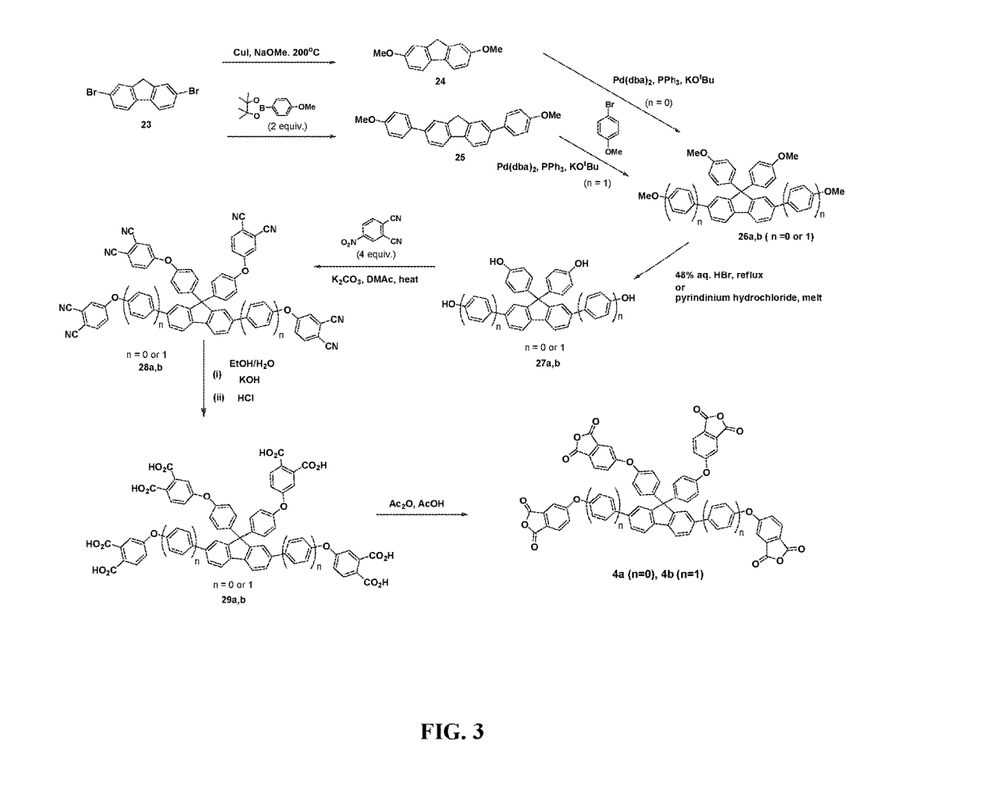
FIG. 3 illustrates an exemplary synthetic scheme toward producing carbon-based tetra-anhydride crosslinking agent 4a,b.

Amenable synthetic sequences toward making crosslinking agents 4a, 4b are provided in FIG. 3. For tetra-anhydride (4a), the synthesis can start with the Ullmann reaction between 2,7-dibromofluorene (23) and excess sodium methoxide and CuI catalyst, preferably in neat mixture form and with high temperature heating (200° C.) to generate the corresponding dimethoxylated fluorene (24). Following a method based on the work of Xiao Cao et al. (*Organic Letters* (2013), 15(12), 3102-3105), 2,7-dimethoxyfluorene (25) is subsequently doubly arylated via $sp^3C$-$sp^2C$ cross-coupling reaction at the C-9 position of fluorene with 4-bromoanisole and the aid of a palladium catalyst in the presence of potassium t-butoxide to afford the corresponding methoxylated spiro-9,9-bifluorene compound 26a (n=0). Then, the tetra-phenol intermediate (27a) can be readily obtained by demethylation with aqueous HBr or pyridinium hydrochloride and heat. A subsequent aromatic nitro-displacement reaction of 4-nitrophthalonitrile (4 equivalents) with the corresponding potassium salt of the tetra-phenol intermediate (27a) leads to the formation of the tetrakis(4-oxyphthalonitrile) compound (28a), which upon hydrolysis is converted to the corresponding tetrakis(4-oxyphthalic acid) precursor (29a). The latter compound, upon treatment with acetic anhydride/acetic acid, leads to the desired carbon-based tetra-anhydride crosslinking agent (4a).

Tetra-anhydride (4b) can be prepared similarly from 2,7-dibromofluorene (23) by following the same synthetic sequence, except for the first (Ullmann reaction) step, which is replaced by a Suzuki cross-coupling reaction with 4-methoxphenylboronic acid or its pinacol boronate ester, a suitable Pd-catalyst, and a base to generate the corresponding 2,7-bis(4-methoxyphenyl)fluorene compound (25).

As also shown in Table 1, the complementary tetra-anhydride crosslinking agents include where W (in Formulas (I), (II), and (IVa)) is silicon or an $sp^3$ hybridized carbon, and thus n is 4. Further, exemplary silicon-based (5a and 5b, E=Si) or $sp^3$ hybridized carbon-based (5c and 5d, E=C) tetra-anhydride crosslinking agents are also shown in Table 1.

Figure 4:
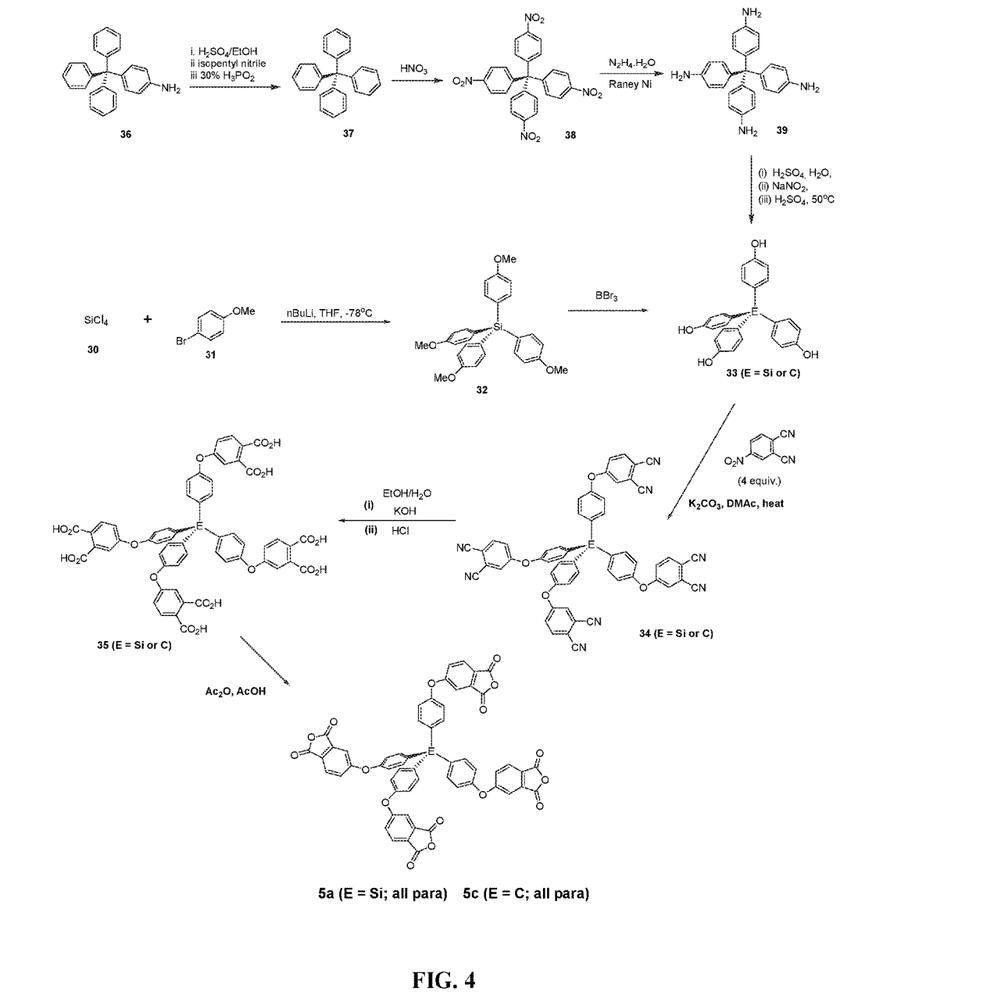
FIG. 4 illustrates an exemplary synthetic scheme toward producing silicon-based and $sp^3$ hybridized carbon-based tetra-anhydride crosslinking agents, 5a and 5c, respectively.

With respect to the silicon-based tetra-anhydride crosslinking agents with four para-phenyleneoxy linkages (5a), an amenable synthetic sequence toward making these agents is shown in FIG. 4. The synthesis of tetra-anhydride (5a) starts with a reaction between tetrachlorosilane (30) and either a Grignard reagent generated from Mg metal and 4-bromoanisole or a lithiated anisole from n-butyllithium and 4-bromoanisole (31) (4 equivalents), following the method of Hao Yu, et al. (*Macromolecules*, 2012, 45(12), 5140-5150). Then, the intermediate (33) (E=Si), i.e. tetrakis (4-hydroxyphenyl)silicon, can be readily obtained by demethylation of tetrakis(4-hydroxyphenyl)silicon (32) with aqueous HBr or pyridinium hydrochloride and heat, or preferably with $BBr_3$ in a chlorinated solvent at room or colder temperature. A subsequent aromatic nitro-displacement reaction of 4-nitrophthalonitrile (4 equivalents) with the corresponding potassium salt of the tetrakis(4-hydroxyphenyl) intermediate (33) leads to the formation of the tetrakis(4-oxyphthalonitrile) compound (34), which upon hydrolysis is converted to the corresponding tetrakis(4-oxyphthalic acid) precursor (35). The latter compound, upon treatment with acetic anhydride/acetic acid leads to the desired silicon-based tetra-anhydride crosslinking agent (5a).

The isomeric (5b) (E=Si, with four meta-phenyleneoxy linkages) can be synthesized following a similar synthetic path except with the substitution of para-phenyleneoxy reagent with the meta-phenyleneoxy reagent in the first of the synthetic scheme shown in FIG. 4. Accordingly, 3-bromoanisole, instead of 4-bromoanisole, is used in the generation of Grignard or aryllithium reagent, which is subsequently reacted with tetrachlorosilane (30).

As shown in FIG. 4, the latter part of the synthetic route from the requisite intermediate (33) (E=C, tetrakis(4-hydroxyphenyl)methane) onward to the carbon-based tetraanhydride, (5c) (E=C), is similar to that for the silicon-based counterparts, (5a) and (5b). Thus, following the method of J. Lu and J. Zhang (Journal of Materials Chemistry A: Materials for Energy and Sustainability (2014), 2(34), 13831-13834), the synthesis of tetrakis(4-hydroxyphenyl)methane starts with the conversion of readily available 4-aminophenyltriphenylmethane (36) to tetraphenylmethane (37) via sequential diazotization reaction with isopentyl nitrile/ $H_2SO_4$ in ethanol, followed by reduction with the aid of hypophosphorous acid. Nitration of tetraphenylmethane, followed by catalytic hydrogenation of the resultant tetrakis (4-nitrophenyl)methane (38) by Raney nickel and hydrazine monohydrate leads to tetrakis(4-aminophenyl)methane (39). Finally, following the method of E. Diez-Barra et al. (Tetrahedron 60 (2004) 1563-1569), diazotization of all the amino groups of 39, followed by acid hydrolysis would provide tetrakis(4-hydroxyphenyl)methane.

Crosslinked Polymers

Because of the similar polymerization chemistry to generate polyimides, polyamides, and poly(amide-imides), the multi-anhydride compounds disclosed herein may be used to crosslink these classes of polymers to create covalent network structures capable of showing shape memory effects at elevated temperatures.

Synthesis of a polyimide is typically accomplished by polymerization of a diamine and a dianhydride in a 1:1 molar ratio to generate a poly(amic acid) precursor, which is then converted to the corresponding polyimide typically by either thermal cure (e.g., by heating to >200° C. in solution or solid state) or chemical imidization using a dehydrating agent or promoter such as acetic anhydride/triethylamine or acetic anhydride/pyridine. To generate a polyimide having the desired amount of crosslinking, an amine-terminated poly(amic acid) precursor is first generated by off-setting the dianhydride:diamine ratio so that the amount of diamine is in excess to cap both ends of the poly(amic acid) precursor. An appropriate amount of a multi-anhydride crosslinking agent is then added to the precursor solution so that all or substantially all of the terminal amine groups will be consumed. Crosslinked polyimides may then be created using appropriate imidization conditions.

In accordance with an aspect of the polymer, the diamine monomer comprises an aromatic diamine, which includes, but is not limited to, 1,3-bis(3-aminophenoxy)benzene (APB); 1,4-bis(3-aminophenoxy)benzene; 1,2-bis(3-aminophenoxy)benzene; 1,2-bis(4-aminophenoxy)benzene; 1,3-bis(4-aminophenoxy)benzene; 1,4-bis(4-aminophenoxy) benzene; 3,4'-oxydianiline; 4,4-oxydianiline; 1,3-diamino-4-methylbenzene; 1,3-diamino-4-(trifluoromethyl)benzene; 2,4-diaminobiphenyl; 2,2-bis(4-aminophenyl)-1,1,1,3,3,3-hexafluoropropane; 2,2-bis(4-aminophenyl)propane; 2,2-bis [4-(4-aminophenoxy)phenyl]-1,1,1,3,3,3-hexafluoropropane; 2,2-bis[4-(4-aminophenoxy)phenyl]propane; or a mixture of thereof.

In accordance with another aspect, the dianhydride monomer includes, but is not limited to 2,2-[bis(4-phthalic anhydrido)]-1,1,1,3,3,3-hexafluoroisopropane (6FDA); 4,4'-oxybis(phthalic anhydride); 3,3',4,4'-diphenylsulfone tetracarboxylic dianhydride; 3,3',4,4'-benzophenone tetracarboxylic dianhydride; 4,4'-(2,2,2-trifluoro-1-phenylethylidene)bis[phthalic anhydride]; 2,2-bis[4-(3,4-dicarboxyphenoxy)phenyl]propane dianhydride; 4,4'-(p-phenylenedioxy) bis[phthalic anhydride]; 4,4'-(m-phenylenedioxy)bis [phthalic anhydride]; 4,4'-(o-phenylenedioxy)bis[phthalic anhydride]; or mixtures thereof.

In accordance with an embodiment, the cross-linked polyimides of the present invention may be defined by the following general chemical formula (VIII):

where W may be P=O, N, Si, or a carbon moiety (e.g., fluorenyl); wherein L denotes either a direct covalent bond to W or a linking group (e.g., a phenyleneoxy group) for indirect bonding to W; n,m,l denote the degree of polymerization (DP) of each branch of polyimide, which may be of the same or different values, with the DP range of about 3 to about 30. For example, in an embodiment, DP is in a range of about 5 to about 25, or about 10 to about 20. The overall network structure is denoted by the infinity symbol (Do). The linking group Y is one of the following moieties: —C(CF_3)_2—, —O—, —SO_2—, —C(=O)—, -(Ph)C (CF_3)—, —OPh-C(CF_3)_2—OPh-, —OPh-C(CH_3)_2—OPh-. In another embodiment, Y is —C(CF_3)_2.

In accordance with another embodiment, the cross-linked polyimides may be defined by the following general chemical formula (IX):

where W may be N or P=O; L, n, m, l, and Y are as defined above.

In accordance with yet another embodiment, the crosslinked polyimides may be defined by the following general chemical formula (X):

where W is N or benzene-1,3,5-trioxy (1,3,5-$C_6H_3O_3$); and n, m, l, and Y are as defined above.

Synthesis of a polyamide is typically accomplished by two general methods. A first method involves polymerization of a diamine and a diacid halide (e.g., chloride) in a 1:1 molar ratio in an amide solvent such as N,N-dimethylformamide (DMF), N,N-dimethylacetamide (DMAc), N-methylpyrrolidone (NMP), etc. However, to generate a polyamide having the desired amount of crosslinking, an amino-terminated polymer is first generated by off-setting the diacid halide:diamine ratio so that the amount of diamine is in excess to cap both ends of the polymer. Subsequent addition of a multi-anhydride crosslinking agent in appropriate amounts to the amino-terminated polymer so that all or substantially all of the terminal amine groups are consumed, immediately followed by casting and thermal curing under reduced pressure, leads to the crosslinked polyamide films.

A second method of synthesizing a polyamide involves polymerization of a diamine and a dicarboxylic acid with the aid of a promoter/catalyst combination such as triethylphosphite/pyridine (via Yamazaki-Higashi reaction) in an amide solvent such as N,N-dimethylformamide (DMF), N,N-dimethylacetamide (DMAc), N-methylpyrrolidone (NMP), etc. However, to generate a polyamide having the desired amount of crosslinking, an amino-terminated polymer is first generated by off-setting the diacid:diamine ratio so that the amount of diamine monomer is in excess to cap both ends of the polymer. After the amino-terminated polyamide has been isolated by precipitation in water and filtration, it is washed (e.g. water and/or methanol) and dried. It is then dissolved in an amide solvent and mixed with an amide solution of a multi-anhydride crosslinking agent in an appropriate amount so that all or substantially all of the terminal amine groups are consumed, which is subsequently followed by casting and thermal curing under reduced pressure to create crosslinked polyamide films.

Similar to the polyimides, the diamine of the polyamides may include, but not limited to, an aromatic diamine, such as 1,3-bis(3-aminophenoxy)benzene (APB); 1,4-bis(3-aminophenoxy)benzene; 1,2-bis(3-aminophenoxy)benzene; 1,2-bis(4-aminophenoxy)benzene; 1,3-bis(4-aminophenoxy)benzene; 1,4-bis(4-aminophenoxy)benzene; 3,4'-oxydianiline; 4,4-oxydianiline; 1,3-diamino-4-methylbenzene; 1,3-diamino-4-(trifluoromethyl)benzene; 2,4-diaminobiphenyl; 2,2-bis(4-aminophenyl)-1,1,1,3,3,3-hexafluoropropane; 2,2-bis(4-aminophenyl)propane; 2,2-bis[4-(4-aminophenoxy)phenyl]-1,1,1,3,3,3-hexafluoropropane; 2,2-bis[4-(4-aminophenoxy)phenyl]propane; or a mixture of thereof. Exemplary diacid halide monomers include, but are not limited to, isophthaloyl chloride; terephthaloyl acid; 4,4'-oxydibenzoyl chloride; 3,4'-oxydibenzoyl chloride; 3,3'-oxydibenzoyl chloride; 4,4'-[2,2,2-trifluoro-1-(trifluoromethyl)ethylidene]bis(benzoyl chloride); 4,4'-(1-methylethylidene) bis(benzoyl chloride); 4,4'-(9H-fluoren-9-ylidene)bis(benzoyl chloride); or a mixture thereof.

Exemplary dicarboxylic acid monomers include, but are not limited to, isophthalic acid, terephthaloyl acid; 4,4'-oxydibenzoic acid; 3,4'-oxydibenzoic acid; 3,3'-oxydibenzoic acid; 4,4'-[2,2,2-trifluoro-1-(trifluoromethyl)ethylidene]bis(benzoic acid); 4, 4'-(1-methylethylidene)bisbenzoic acid; 4,4'-(9H-fluoren-9-ylidene)bis(benzoic acid); or a mixture thereof.

Figure 5:
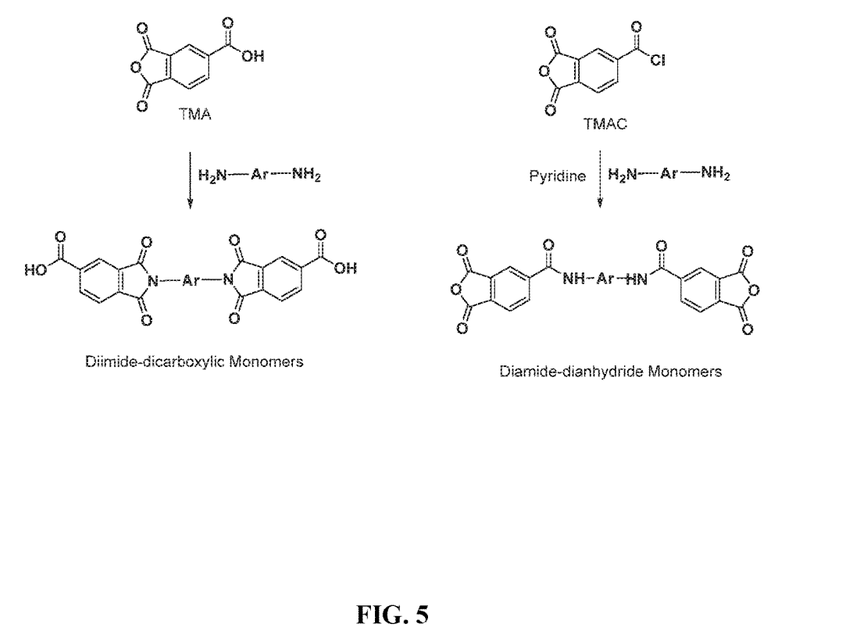
FIG. 5 illustrates exemplary synthetic schemes toward producing diimide-dicarboxylic acid monomers and diamide-dianhydride monomers useful for synthesizing poly(amide-imide)s.
Figure 6:
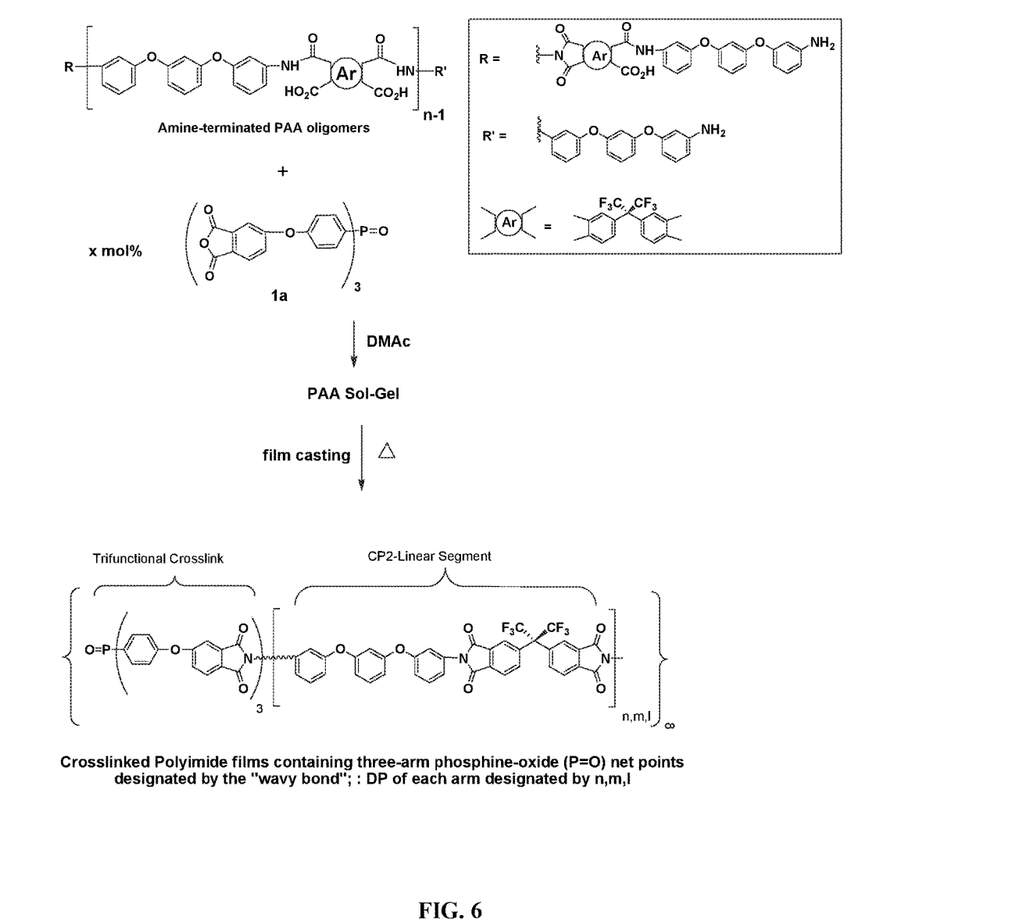

The synthesis of a poly(amide-imide) is typically accomplished by polymerization of i) a diamine and a trimellitic anhydride (TMA) or trimellitic anhydride acid chloride (TMAC); or ii) a diamine and a diimide-dicarboxylic acid monomer derived from a selective condensation of TMA and an aromatic diamine (e.g., $H_2N$—Ar—$NH_2$) (see FIG. 5). When acid monomers are used, the polymerization process is aided by triethylphosphite/pyridine (Yamazaki-Higashi reagent) in a 1:1 molar ratio in an amide solvent such as N,N-dimethylformamide (DMF), N,N-dimethylacetamide (DMAc), N-methylpyrrolidone (NMP), etc.

Persons having ordinary skill in the art will appreciate that these polymerization methods may be applied to other dianhydride monomers containing preformed aromatic amide moieties. For example, bis(phthalic anhydride) monomers with preformed amide as part of the linking group, which are also known as diamide-dianhydrides, can be prepared from trimellitic anhydride acid chloride (TMAC) and an aromatic diamine (e.g., $H_2N$—Ar—$NH_2$) in refluxing acetone with pyridine as HCl scavenger (see FIG. 5).

However, to generate a poly(amide-imide) having the desired amount of crosslinking, it is more suitable that an amino-terminated poly (amide-imide) is first generated via Yamazaki-Higashi reaction by off-setting TMA:diamine ratio so that the amount of diamine is in excess to cap both ends of the polymer. After the amino-terminated polyamide has been isolated by precipitation in methanol and filtration, it is washed with methanol and dried (e.g., in vacuo at 200° C. overnight). The amino-terminated polyamide is then dissolved in an amide solvent and mixed with an amide solution of a multi-anhydride crosslinking agent in an appropriate amount so that all or substantially all of the terminal amine groups are consumed, which is immediately followed by casting and thermal curing under reduced pressure to create crosslinked poly(amide-imide) films.

The following examples and methods are presented as illustrative of the present invention or methods of carrying out the invention, and are not restrictive or limiting of the scope of the invention in any manner.

EXAMPLES

Example 1

Tris(4-methoxyphenyl)phosphine Oxide (13a)

Into a 100 mL three-necked flask equipped with a magnetic stir bar and nitrogen inlet and outlet were placed commercially available tris(4-methoxyphenyl)phosphine ((12a), 3.0 g, 8.5 mmol) and acetone (30 mL). A mixture of water (2 mL) and $H_2O_2$ (35%, 1 mL, 9 mmol) was added slowly. After the mixture was stirred at room temperature for 1 h, acetone was evaporated and methylene chloride (50 mL) was added. The organic phase was washed with a saturated NaCl solution (35 mL) three times. The organic layer was dried over sodium sulfate. The solvent was removed under vacuum to afford 3.0 g (95%) of a white solid, m.p. 144.7-145.4° C. (lit. 143-144° C.). MS (m/e): 368 ($M^+$). Anal. Calcd. for $C_{21}H_{21}O_4P$: C, 68.47%; H, 5.75%; P, 8.41%. Found: C, 68.42%; H, 5.72%; P, 8.11%. FT-IR (KBr, $cm^{-1}$): 3068, 3026, 2959, 2837, 1597, 1569, 1503, 1468, 1289, 1254, 1179, 1121, 1019, 803, 671, 543. $^1$H-NMR ($CDCl_3$, δ in ppm): 3.84 (s, 6H, $CH_3$), 6.94-6.97 (dd, 6H, Ar—H), 7.54-7.60 (dd, 6H, Ar—H). $^{13}$C-NMR (DMSO-$d_6$, δ in ppm): 55.29, 114.08, 114.21, 124.19, 125.28, 133.21, 133.32, 161.79, 161.822

Example 2

Tris(4-hydroxyphenyl)phosphine Oxide (14a)

Into a 500 mL 3-neck round bottom flask equipped with stir bar, nitrogen inlet and condenser was charged tris(4-methoxyphenyl)phosphine oxide ((13a), 25.0 g, 67.9 mmol) followed by pyridine hydrochloride (250 g). The mixture was heated to 210° C. for 2 hours and allowed to cool to about 100° C. It was poured into water to afford 21.0 g (95.0%) of white crystals. m.p.: 274.8-276.8° C. (lit. 275-276° C.). The product was used without further purification. Anal. Calcd. for $C_{18}H_{15}O_4P$: C, 66.26%; H, 4.63%; P, 9.49%; Found: C, 65.72%; H, 4.68%; P, 9.59%. $^1$H-NMR (DMSO-$d_6$, δ in ppm): 6.84-6.86 (dd, 6H, Ar—H), 7.30-7.45 (dd, 6H, Ar—H), 10.07 (s, 3H, Ar—O—H). $^{13}$C-NMR (DMSO-$d_6$, δ in ppm): 115.32, 115.45, 122.59, 123.69, 133.29, 133.40, 160.28, 160.30.

Example 3

Tris[4-(3,4-dicyanophenoxy)phenyl]phosphine Oxide (16a)

Into a 500 mL 3-neck round bottom flask equipped with stir bar, condenser, and nitrogen inlet were charged tris(4-hydroxyphenyl)phosphine oxide ((14a) 8.13 g, 25.0 mmol), 4-nitrophthalonitrile ((15), 13.0 g, 75.0 mmol), $K_2CO_3$ (11.5 g, 85.5 mmol), and DMF (150 mL). The mixture was heated at 50° C. for 24 h. Then it was poured into distilled water. The organic layer was extracted with ethyl acetate 3 times and dried over magnesium sulfate. The mixture was filtered and the filtrate was dried on a rotary evaporator afford 15.8 g (81%) of a yellow powder. m.p. 205.0-206.6° C. m.p. 127.6-132.8° C. The yellow powder was further purified by slurrying in ethyl acetate. m.p. 138.1-139.4° C. Anal. Calcd. for $C_{42}H_{21}N_6O_4P$: C, 71.59%; H, 3.00%; N, 11.93%. Found: C, 71.41%; H, 2.99%; N, 11.59%. $^1$H-NMR (DMSO-$d_6$, δ in ppm): 7.33-7.35 (dd, 6H, Ar—H), 7.54-7.57 (dd, 3H, Ar—H), 7.73-7.78 (dd, 6H, Ar—H), 7.95-7.96 (d, 3H, Ar—H) 8.14-8.16 (d, 3H, Ar—H). $^{13}$C-NMR (DMSO-$d_6$, δ in ppm): 109.40, 115.28, 115.77, 116.87, 119.78, 119.90, 128.47, 129.53, 134.19, 134.30, 136.30, 136.40, 157.41, 157.44, 159.59.

Example 4

Tris[4-(3,4-dicarboxyphenoxy)phenyl]phosphine Oxide (17a)

Into a 250 mL 3-neck round bottom flask equipped with stir bar, condenser, and nitrogen inlet were charged tris[4-(3,4-dicyanophenoxy)phenyl]phosphine oxide ((16a), 2.5 g, 3.2 mmol), KOH (2.7 g, 48 mmol), and ethanol/water (1:1, 60 mL). The mixture was heated under reflux for 12 h until it formed a clear solution. The solution was allowed to cool to room temperature and neutralized with conc. HCl solution to pH 1-3. The white precipitate was collected and dried in oven to afford 2.60 g (99%) of white crystals. m.p.>300° C. $^1$H-NMR (DMSO-$d_6$, δ in ppm): 7.22-7.27 (m, 12H, Ar—H), 7.67-7.72 (dd, 6H, Ar—H), 7.76-7.78 (d, 3H, Ar—H). $^{13}$C-NMR (DMSO-$d_6$, δ in ppm): 118.35, 118.90, 119.02, 120.51, 127.35, 127.40, 128.46, 131.40, 134.02, 134.13, 136.46, 157.46, 158.83, 158.86, 167.52, 168.21.

Example 5

Tris[4-(3,4-dicarboxyphenoxy)phenyl]phosphine oxide tri-anhydride (1a)

Into a 100 mL 3-neck round bottom flask equipped with stir bar, condenser, and nitrogen inlet were charged tris[4-(3,4-dicarboxyphenoxy)phenyl]phosphine oxide ((17a), 2.0 g, 2.44 mmol), acetic acid (7 mL), and acetic anhydride (15 mL). The mixture was refluxed for 4 h until it formed a clear solution, which was then filtered while hot to remove insoluble impurities. After cooling to room temperature, the crystallized solid was collected, washed with dry toluene, and dried under vacuum to afford 1.4 g (75%) of golden yellow crystals. m.p. 151.8-152.1° C. Anal. Calcd. for $C_{42}H_{21}O_{13}P$: C, 65.98%; H, 2.77%; N, 0%; P, 4.05%. Found: C, 65.34%; H, 2.91%; N, <0.1%; P, 3.94. $^1$H-NMR (DMSO-$d_6$, δ in ppm): 7.34-7.36 (dd, 6H, Ar—H), 7.62-7.65 (dd, 3H, Ar—H), 7.66-7.68 (dd, 3H, Ar—H), 7.77-7.82 (dd, 6H, Ar—H), 8.01-8.12 (d, 3H, Ar—H). $^{13}$C-NMR (DMSO-$d_6$, δ in ppm): 114.48, 119.75, 119.88, 125.95, 125.98, 127.94, 128.39, 129.44, 134.18, 134.26, 134.37, 157.92, 157.95, 162.29, 162.40, 162.47.

Example 6

Representative procedure for the synthesis of trianhydride-crosslinked polyimides (2 mol % tri-anhydride, PAn-CP2-2). 1,3-bis(3-aminophenoxy)benzene ((APB), 1.169 g, 4.000 mmol) and DMAc (15 mL) were added to a 50 mL 3-necked flask equipped with a magnetic stirrer, nitrogen inlet and outlet, and stirred under dry nitrogen at room temperature for 30 min. 2,2-[bis(4-phthalic anhydride)]-1,1,1,3,3,3-hexafluoroisopropane ((6FDA), 1.724, 3.880 mmol) was then charged. The light yellow solution was agitated at room temperature for about 24 hr to afford a poly(amic acid) solution. Then the tri-anhydride crosslinking agent ((1a), 0.0612 g, 0.080 mmol) was added to this solution. After the tri-anhydride crosslinking agent was totally dissolved in DMAc, the mixture was poured into a glass dish, followed by vacuum evaporation of DMAc at 50° C., and heat-treated sequentially at: 100° C./1 h, 150° C./1 h, 175° C./1 h, 200° C./1 h, 250° C./1 h, and 300° C./1 h to form crosslinked polyimide films. The film thickness of the crosslinked polyimide film was in a range of approximately 20 to approximately 100 μm. This general procedure was followed to prepare other PAn-CP2-x (x stands for mole percentage of tri-anhydride crosslinking agent.

Example 9

TABLE 2

Composition and properties of polyimide films

| Sample | 6FDA (mol %) | APB (mol %) | Trianhydride (1a) (mol %) | Tg (° C.) | $E^b$ (GPa) | $T_{d5\%}^{c}$ (° C.) in air | $M_c^d$ | Gel Content$^{e,g}$ | Swelling Ratio$^{f,g}$ |
|---|---|---|---|---|---|---|---|---|---|
| Linear CP2$^d$ | 100 | 100 | 0 | 219 | 1.90 ± 0.15 | 526 | — | — | — |
| PAn-CP2-0.5 | 99.75 | 100 | 0.5 | 219 | 2.03 ± 0.32 | 514 | 140,150 | 62.1 | 17.2 |
| PAn-CP2-1 | 98.5 | 100 | 1 | 220 | 2.18 ± 0.27 | 519 | 46,800 | 91.9 | 5.5 |
| PAn-CP2-2 | 97.0 | 100 | 2 | 222 | 2.54 ± 0.19 | 518 | 23,460 | 94.4 | 4.7 |
| PAn-CP2-5 | 92.5 | 100 | 5 | 232 | 2.84 ± 0.32 | 518 | 9,460 | 97.7 | 3.1 |

(a) Tg measured from the peak of tan delta (DMA) as an average value taken from 4 measurements;
(b) Modulus determined in tension at 25° C. as average from 5 specimens per sample;
(c) Temperature at which 5 wt % loss as determined by TGA at a heating rate of 10° C./min;
(d) $M_c$ is the theoretical molecular weight of chains between crosslinks;
(e) Gel Content = Wi/Wx × 100%;
(f) Swelling Ratio = Wg/Wx × 100%.
(g) Test procedure for (e) and (f): Films weighed at room temp (Wi). Films immersed in DMAc (2 days). Gel rinsed in fresh DMAc (2X) to remove soluble fractions, wiped with tissue paper and weighed (Wg). Gel heat-treated in an oven at 300° C. Crosslinked CP2 weighed at room temperature (Wx).

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

What is claimed is:

1. A multifunctional crosslinking agent comprising a plurality of anhydride functional groups, and defined by a chemical formula (I):

(Z—Ar)$_n$—W           (I)

wherein Z represents an anhydride functional group that is directly bonded to Ar;
Ar represents an aryl-ether group that is directly bonded to W; and
n is equal to 3 when W is P=O or N, or n is equal to 4 when W is Si or a carbon moiety.

2. The multifunctional crosslinking agent of claim 1, wherein W is P=O.

3. The multifunctional crosslinking agent of claim 1, wherein W is N.

4. The multifunctional crosslinking agent of claim 1, wherein W is the carbon moiety.

5. The multifunctional crosslinking agent of claim 1, wherein W is Si.

6. The multifunctional crosslinking agent of claim 1, wherein Ar is an oxyphenylene group (—OPh-) that is para- or meta-substituted with respect to oxygen, and the agent is further defined by a formula (II):

(Z—OPh)$_n$-W.

7. The multifunctional crosslinking agent of claim 1, wherein Z is an aromatic anhydride.

8. The multifunctional crosslinking agent of claim 7, wherein the aromatic anhydride is a phthalic anhydride or a naphthalic anhydride.

9. The multifunctional crosslinking agent of claim 1, wherein Ar is an oxyphenylene group (—OPh-) that is para- or meta-substituted with respect to oxygen, and wherein Z is a phthalic anhydride group that is connected to the oxyphenylene group through an ether bond.

10. The multifunctional crosslinking agent of claim 1, wherein W is P=O, wherein Ar is an oxyphenylene group (—OPh-) that is para- or meta-substituted with respect to oxygen, and wherein the agent is further defined by a formula (III):

(Z—OPh)$_3$-P=O.

11. The multifunctional crosslinking agent of claim 10, wherein Z is a phthalic anhydride group that is connected to the oxyphenylene group through the ether bond, and wherein the agent is further defined by a formula (IV):

wherein $R^1$ through $R^8$ are independently selected from H or C1-C4 alkyl.

12. The multifunctional crosslinking agent of claim 11, wherein the agent is selected from tris[3-(3,4-dicarboxyphenoxy)phenyl]phosphine oxide trianhydride or tris[4-(3,4-dicarboxyphenoxy)phenyl]phosphine oxide trianhydride.

13. The multifunctional crosslinking agent of claim 1, wherein W is N, wherein Ar is an oxyphenylene group (—OPh-) that is para- or meta-substituted with respect to oxygen, and wherein the agent is further defined by a general formula (V):

(Z—OPh)$_3$-N.

14. The multifunctional crosslinking agent of claim 13, wherein Z is a phthalic anhydride group that is connected to the oxyphenylene group through the ether bond, and wherein the agent is further defined by a general formula (VI):

wherein $R^1$ through $R^8$ are independently selected from H or C1-C4 alkyl.

15. The multifunctional crosslinking agent of claim 14, wherein the agent is selected from tris[3-(3,4-dicarboxyphenoxy)phenyl]amine trianhydride or tris[4-(3,4-dicarboxyphenoxy)phenyl]amine trianhydride.

16. A crosslinked polymer composition comprising an amino-terminated polymer selected from a polyamide, a polyimide, a poly(amide-imide), or mixtures thereof, which is cross-linked by the multifunctional cross-linking agent of claim 1.

17. The crosslinked polymer composition of claim 16, wherein the polyamide is a polymerization reaction product of a diamine with a dicarboxylic acid, a diacid halide, or a combination thereof; and wherein the diamine is reacted in a stoichiometric excess relative to the dicarboxylic acid, the diacid halide, or a sum total of the combination thereof.

18. The crosslinked polymer composition of claim 16, wherein the polyimide is a polymerization reaction product of a diamine with a dianhydride; and wherein the diamine is reacted in a stoichiometric excess relative to the dianhydride.

19. The crosslinked polymer composition of claim 16, wherein the polyimide is a polymerization reaction product of a diamine with
  1) a trimellitic anhydride, a diacid derivative of trimellitic acid, or trimellitic acid, or
  2) a dianhydride, and a dicarboxylic acid, a diacid halide, or a combination thereof; and wherein the diamine is reacted in a stoichiometric excess relative to a sum total of 1) or 2).

20. The crosslinked polymer composition of claim 16, wherein the poly(amide-imide) is a polymerization reaction product of a diamine with 1) diimide-dicarboxylic acid monomer, and/or 2) a diamide-dianhydride monomer.

* * * * *